(12) United States Patent
Hook et al.

(10) Patent No.: US 11,766,504 B1
(45) Date of Patent: Sep. 26, 2023

(54) THREE-DIMENSIONAL FACEMASK WITH ULTRAVIOLET LIGHT AND RAIN HOOD

(71) Applicants: Steven Russell Hook, Silver Spring, MD (US); Richard W Hook, Silver Spring, MD (US)

(72) Inventors: Steven Russell Hook, Silver Spring, MD (US); Richard W Hook, Silver Spring, MD (US)

( * ) Notice: Subject to any disclaimer, the term of this patent is extended or adjusted under 35 U.S.C. 154(b) by 0 days.

(21) Appl. No.: 18/095,074

(22) Filed: Jan. 10, 2023

(51) Int. Cl.
*A61L 9/20* (2006.01)
*A41D 13/11* (2006.01)

(52) U.S. Cl.
CPC ............ *A61L 9/20* (2013.01); *A41D 13/1138* (2013.01); *A41D 13/1161* (2013.01); *A61L 2209/14* (2013.01)

(58) Field of Classification Search
CPC .... A41D 13/11–1192; A62B 23/00–04; A62B 18/00–10; A62B 7/00–14; A62B 9/00–06; A61M 16/06–0694; A61L 9/00; A61L 9/16–20; A61L 2209/00; A61L 2209/10; A61L 2209/14
See application file for complete search history.

(56) References Cited

U.S. PATENT DOCUMENTS 11,000,624 B1 * 5/2021 Babcock ................... A61L 9/20
11,213,080 B2 1/2022 Henderson 2005/0098180 A1 5/2005 Lien et al.
2012/0279503 A1 * 11/2012 Zhou ................... A41D 13/1192
128/205.27
2021/0162089 A1 6/2021 Zimmermann et al.
2021/0338878 A1 11/2021 Buskirk

FOREIGN PATENT DOCUMENTS

CN 111213937 A * 6/2020
KR 20110045783 A * 5/2011

* cited by examiner

*Primary Examiner* — Michelle J Lee
(74) *Attorney, Agent, or Firm* — Dale J. Ream

(57) ABSTRACT

A face mask assembly includes a body shell having walls arranged in a three-dimensional configuration having an open back and interior area partially air impermeable. The front wall includes a vent portion permeable to airflow. An outer shell includes walls coupled in a polygonal configuration defining an open back and interior area that receives the body shell. The outer shell walls are permeable to an ambient airflow. A rain shield having moisture impermeable walls has a configuration complementary to that of the outer shell and is releasably coupled to a front surface of the outer shell, such as with embedded complementary magnets or eyelet openings. The facemask assembly includes an ultraviolet ("UV") light assembly in the body interior area adjacent the vent portion, or in the interior of the rain shield and adjacent the vent portion, the UV light assembly producing electromagnetic energy capable of suppressing germs when actuated.

17 Claims, 10 Drawing Sheets

THREE-DIMENSIONAL FACEMASK WITH ULTRAVIOLET LIGHT AND RAIN HOOD

BACKGROUND OF THE INVENTION

This invention relates generally to disinfecting facemask assemblies and, more particularly, a facemask having an ultraviolet light, a three-dimensional structure, and a rain shield.

The main role of a facemask worn over the nose and mouth of a user is to prohibit, minimize, or purify ambient air being inhaled by a human wearer. A traditional facemask has a planar and flexible configuration constructed of a fabric material configured to capture or block particles containing an infection or a virus. Other facemask assemblies include filters, some including activated carbon.

Although presumably effective for their intended purposes, the existing devices and proposals smother the user's face and are worn with ear straps, which are objectionable to some people and can interfere with hearing aids. They, remain inadequate to focus an incoming stream of ambient air and subject that focused airstream to ultraviolet light or alternative types of filtration, whereby to kill virus or infectious components. In addition, the existing devices invariably fail to fit a user's face and a failure to maintain a proper position leads to failure altogether, as well as fogging the glasses.

Therefore, it would be desirable to have a three-dimensional facemask assembly that includes a polygonal configuration that promotes a comfortable and secure position on a wearer's nose and face. Further, it would be desirable to have a three-dimensional facemask assembly having a vent portion that allows an incoming airstream and an ultraviolet light assembly configured to subject that incoming airstream to an ultraviolet light. In addition, it would be desirable to have a three-dimensional facemask assembly that includes a rain shield, whereby its underlying and functional structures are shielded from weather events.

SUMMARY OF THE INVENTION

A three-dimensional face mask assembly according to the present invention includes a body shell having bottom, top, and front walls arranged in a three-dimensional polygonal configuration, the bottom and top walls, and a portion of the front wall being constructed of a material that is impermeable to ambient air. The body walls, together, define an open rear end and a body interior area. The body front wall includes a vent portion that extends laterally between opposed ends of the body front wall and that is permeable to ambient airflow.

The facemask assembly includes an outer shell having bottom, top, and front walls coupled together in a three-dimensional polygonal configuration. The outer shell walls, together, define an open outer shell rear end and an outer shell interior area that is configured to receive the body shell in a nested arrangement. The outer shell walls are constructed of a fabric material that is permeable to an ambient airflow.

In an embodiment, the facemask assembly includes a rain shield having a center panel and a pair of shield side sections each being angled rearwardly and outwardly away from the center panel, the rain shield having a configuration that is complementary to a configuration of the outer shell and is releasably coupled to a front surface of the outer shell, such as embedded complementary magnets or complementary eyelet openings. The rain shield walls are constructed of a water impermeable material. In an embodiment, the facemask assembly includes an ultraviolet ("UV") light assembly positioned in the body interior area adjacent the vent portion, the UV light assembly being operable to produce electromagnetic energy capable of suppressing germs when actuated.

Therefore, a general object of this invention is to provide a three-dimensional face mask assembly, as aforesaid, that is operable to kill germs in an ambient airflow passing into the facemask of a wearer.

Another object of this invention is to provide a three-dimensional face mask assembly, as aforesaid, having an ultraviolet light assembly.

A further object of this invention is to provide a three-dimensional face mask assembly, as aforesaid, having variable and scalable filtration assemblies such as activated charcoal, non-woven polypropylene, or wicking materials.

Still another object of this invention is to provide a three-dimensional face mask assembly, as aforesaid, having a moisture impermeable rain hood that is configured to shield a facemask from weather elements.

Yet another object of this invention is to provide three-dimensional face mask assembly, as aforesaid, that includes embedded magnets to enhance a coupling of respective rain hood and shell portions.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

Fig. 1b is a reverse perspective view of the facemask assembly as in Fig. 1a;

FIG. 3a is an exploded view of the facemask assembly as in Fig. 1a;

FIG. 4b is a reverse perspective view of the facemask assembly as in FIG. 4a;

FIG. 5 is an exploded view of the facemask assembly as in Fig. 1a;

FIG. 6a is a front view of the facemask assembly as in Fig. 1a;

FIG. 6b is a sectional view taken along line 6b-6b of FIG. 6a;

FIG. 7b is a top view of the ultraviolet light assembly as in FIG. 7a;

FIG. 8a is a perspective view of the ultraviolet light assembly as an FIG. 7a;

FIG. 8b is an isolated view on an enlarged scale taken from FIG. 8a;

FIG. 9a is a rear view of the ultraviolet light assembly as in FIG. 7a;

FIG. 9b is an isolated view on an enlarged scale taken from FIG. 9a; and

DESCRIPTION OF THE PREFERRED EMBODIMENT

A three-dimensional ultraviolet light facemask assembly (hereafter referred to as "the facemask assembly") according to a preferred embodiment of the present invention will now be described with reference to Fig. 1a to 10 of the accompanying drawings. The facemask assembly 10 includes a body shell 20, and outer shell 30, an ultraviolet light assembly 40, and a rain shield 50.

The facemask assembly 10 is a multi-layered assembly that, when worn on a user's face, enables an ambient airstream to flow freely through a front layer and then to be focused for contact with an ultraviolet light prior to being inhaled by the user. More particularly, the facemask assembly 10 includes an outer shell 30 that includes a plurality of walls arranged in a three-dimensional or polygonal configuration and constructed of a flexible material that is permeable to ambient air. For instance, the outer shell 30 may be constructed of a fabric material that is air permeable although the outer shell 30 may include a stiffener or framework that arranges the fabric into a plurality of walls. For instance, the outer shell 30 may include a bottom wall (referred to as an outer shell bottom wall 31 and a top wall (referred to as an outer shell top wall 32) that is, at least in one configuration, parallel to the bottom wall of the outer shell 30. Further, the outer shell 30 may also include a front wall (also referred to as an outer shell front wall 33) that extends between front and side edges of the outer shell bottom wall 31 and outer shell top wall 32, respectively. Preferably, the outer shell bottom wall 31, outer shell top wall 32, and outer shell front wall 33, in combination, include rear edges, respectively, that define an outer shell open rear end and define an outer shell interior area that is configured and dimensioned to receive the body shell 20 therein in a nested relationship as will be discussed in more detail below. The outer shell 30 is in many ways constructed as a traditional fabric facemask although it may include a stiffener or be sewn together in such a manner that enables it to include a three-dimensional shape configuration of the more rigid body shell 20 that is nested inside the interior area of the outer shell 30, as will be discussed below in more detail.

Figure 1A:
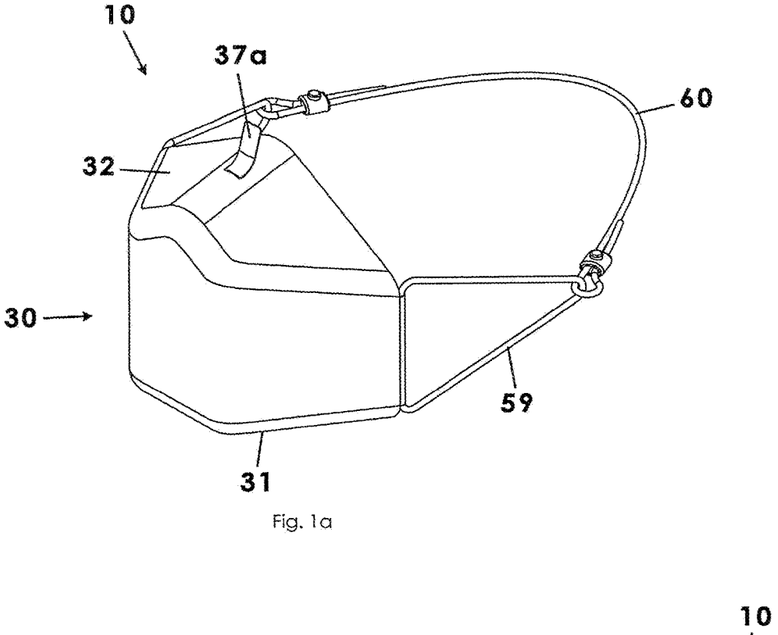
Fig. 1a is a perspective view of a three-dimensional facemask assembly according to a preferred embodiment of the present invention.
Figure 1B:
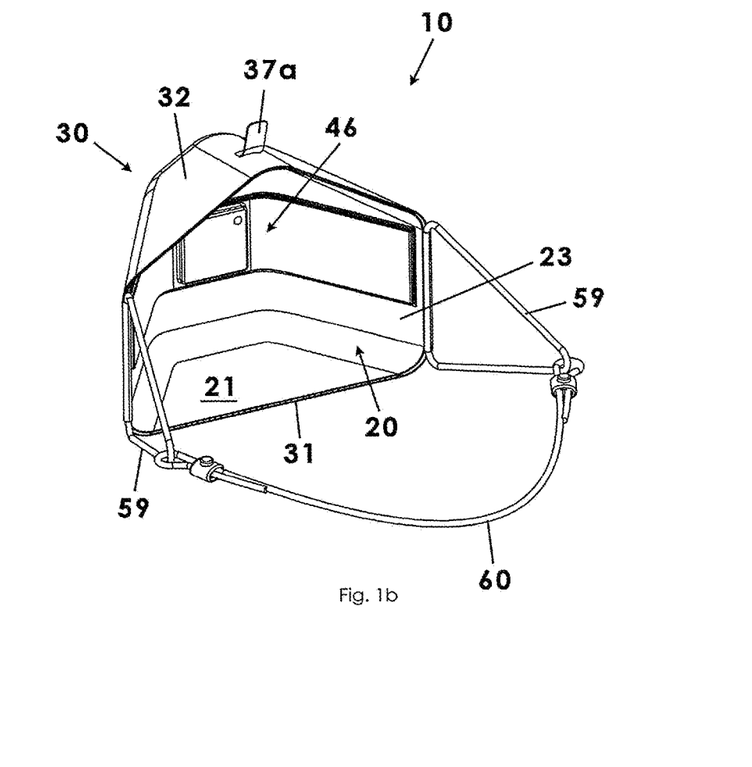

In an important aspect, the outer shell top wall 32 has a flexible or semi-flexible construction so as to be movable between a retracted or generally planar configuration and an upwardly extended or elevated configuration. More particularly, the outer shell top wall 32 includes a pull tab 37a, such as may be constructed of fabric material mounted to an upper surface of the outer shell top wall 32. In use, the pull tab 37a may be grasped by a hand of a user so as to pull the outer shell top wall 32 upwardly. In addition, the rearward edge of the outer shell top wall 32 may include a nose-fit member 37b constructed of a spring steel wire configured to hold the outer shell top wall 32 in the upward configuration once pulled upwardly. At the upward configuration, the outer shell top wall 32 may be referred to as having an inverted V-shaped configuration (Fig. 1b). Further still, it will be understood that if the outer shell 30 and body shell 20 adhered together, such as by glue or sewing, then the body shell top wall 22 will be analogously pulled upwardly when the pull tab 37a is pulled upwardly as is apparent in Figs. 1b and 4b.

The body shell 20 of the facemask assembly 10 is preferably constructed of a semi-rigid material such as PVC plastic or the like that is molded or otherwise assembled in a three-dimensional polygonal shape configuration that, in use, will be comfortable and secure when placed over a wearer's nose and mouth. More particularly, the body shell 20 may include a body bottom wall 21, a body top wall 22 that is, at least when at a relaxed configuration, generally parallel to the body bottom wall 21. Further, the body shell 20 may include a body front wall 23 extending between forward edges of the body bottom wall 21 and body top wall 22. Probably, the body bottom wall 21, the body top wall 22, and body front wall 23 each include rearward edges that, together, define an open rear end and body interior area. Further details regarding the actual configuration of the walls will be discussed later. Preferably, the body shell 20 is constructed of a material that is rigid or semi-rigid and impermeable by ambient air. For instance, each of the walls of the body shell 20 may be constructed of a nonporous material such as plastic, glass, vinyl, leather, or the like, except as noted below.

Figure 3A:
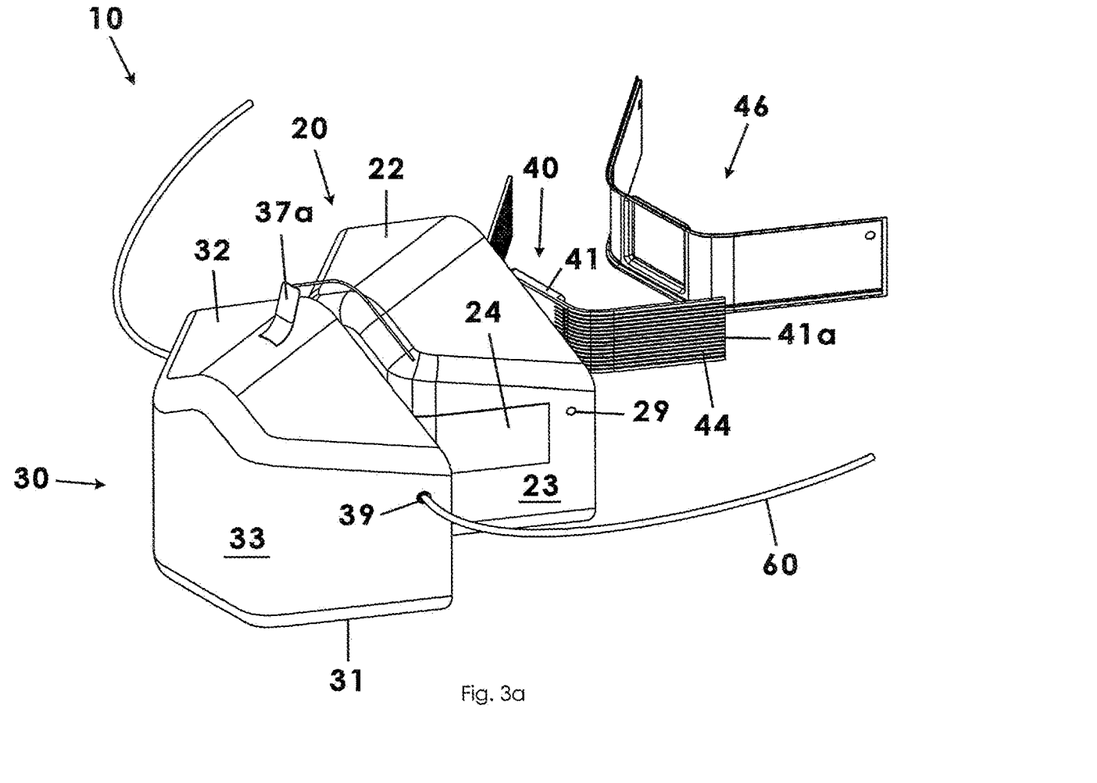
Figure 5:
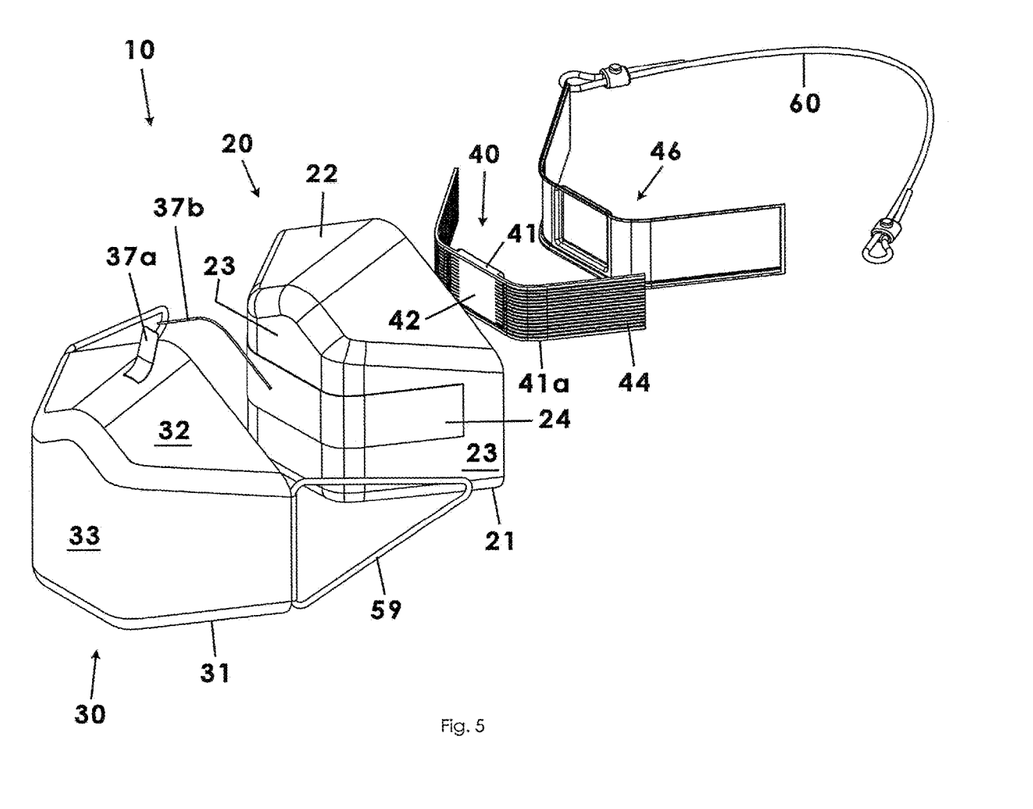
Figure 6A:
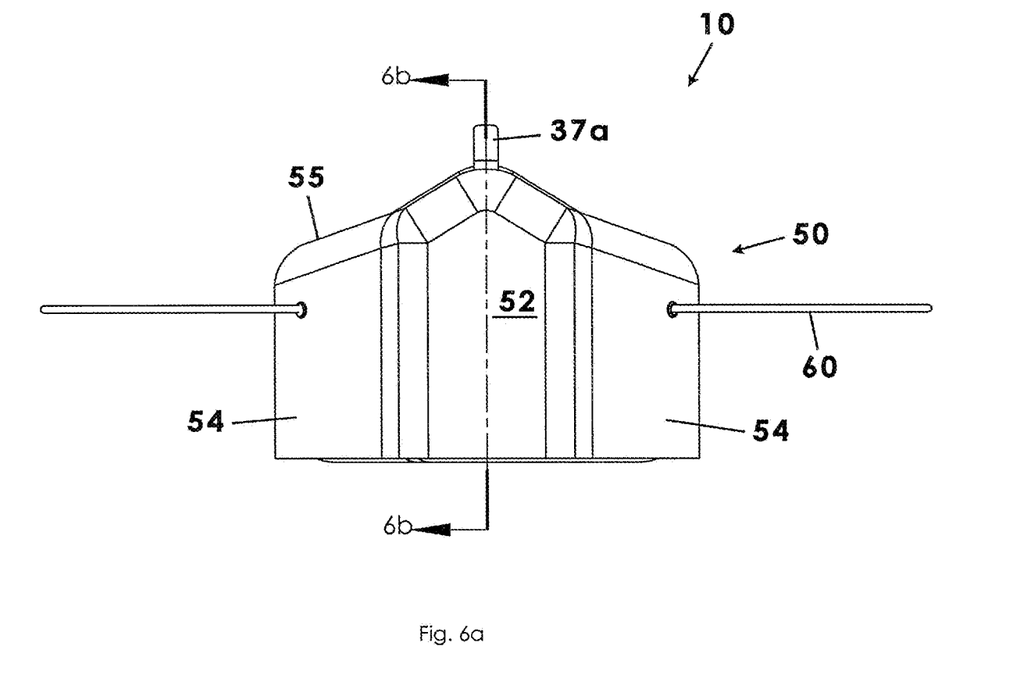
Figure 6B:
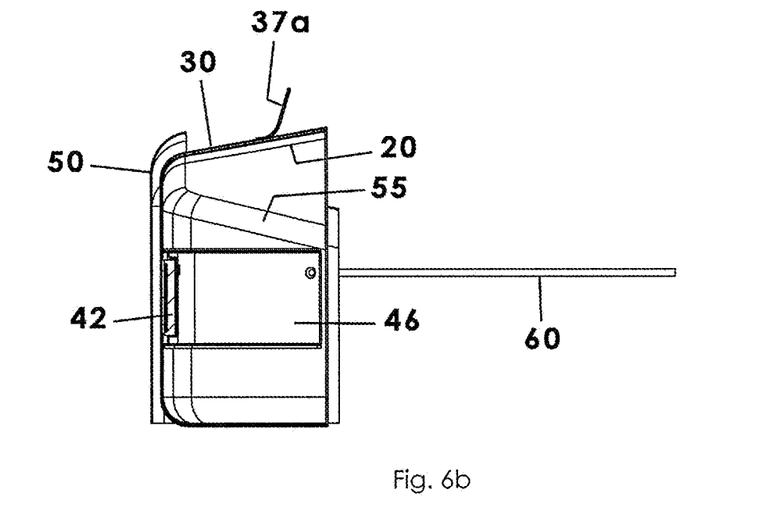

In a critical aspect, the body front wall 23 may include a vent portion 24 that is constructed of an air permeable or porous material, such as a mesh or screen material. In an embodiment, the vent portion may have a rectangular configuration extending laterally substantially between opposed rearward ends of the front wall 23 (FIG. 3a). The vent portion 24 has a vent front section and a pair of vent side sections angled rearwardly and outwardly away from said vent front section to coincide with the body front section and pair of body side sections, respectively, as seen in FIGS. 1b and 5. In use, an airstream may pass through the porous outer shell 30 but is then focused and allowed to pass through the vent portion 24 of the body shell 20.

Preferably, the outer shell 30 and body shell 20 have configurations that are substantially concentric, i.e., have substantially the same shape configurations although the dimensions of the outer shell 30 may be slightly larger than those of the body shell 20 such that a front surface of the body shell 20 may be coupled to a rear surface of the outer shell 30, such as being coupled with glue or the like. In other words, the open interior area of the outer shell is configured to receive the walls of the body shell 20 in a nested configuration. This permits the main structure 20 to accommodate various fabric or style choices of the wearer.

Further description of the specific configurations of the walls of the body shell 20 and outer shell 30 will be given. First, the body bottom wall 21, body top wall 22, and body front wall 23 each include rear edges, respectively, that together form a configuration that can cover a nose of a human person wearing the facemask assembly 10. Second, the body front wall 23 may include a body front section 23a and a pair of body side sections 23b that are each angled rearwardly and outwardly away from the body front section 23a. Stated another way, the body front wall 23 has what may be described as angled sidewalls or wings. It will be understood that the body bottom wall 21 and top wall 22 have complementary configurations extending fully between bottom and top edges of the opposed side sections 23b, respectively (FIG. 3a). Without specifically describing it, it is understood that the walls of the outer shell are complementary and concentric to those of the body shell as described above and, therefore, may include analogous front and side sections.

In another critical aspect, the facemask assembly 10 may include an ultraviolet light assembly 40 (which may also be referred to as a UV light assembly or just a UV assembly).

Figure 4A:
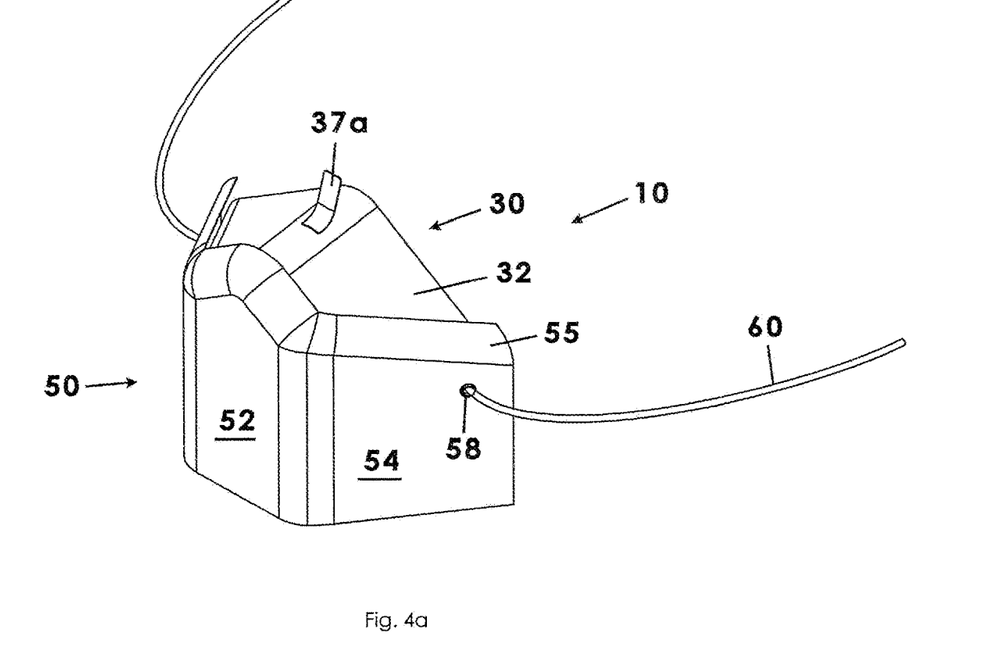
FIG. 4a is a perspective view of the rain shield coupled to the outer shell according to the present invention.
Figure 4B:
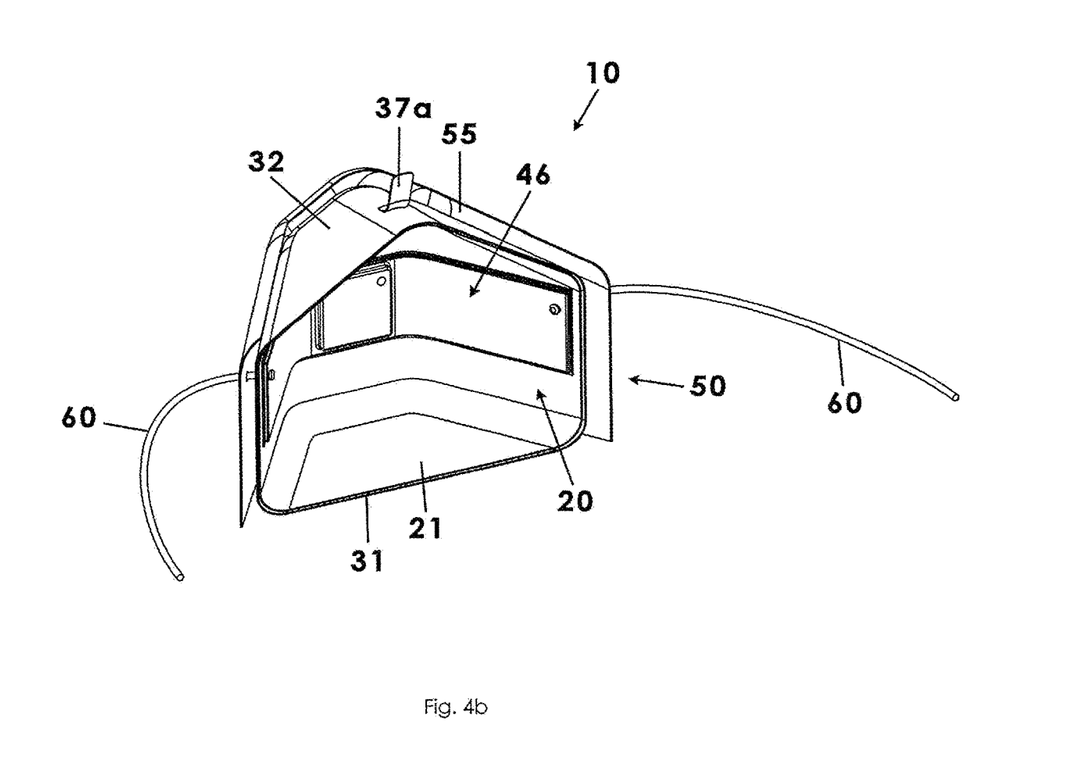

In general, the UV light assembly is positioned inwardly adjacent the vent portion 24 of the body shell 20 or, alternatively, positioned inwardly adjacent the rainhood so as to irradiate all incoming ambient air prior to arrival at the vent portion 24 of the body shell 20, which in an embodiment, includes the pull tab, nose spring steel feature, and ear/neck strap features without the inclusion of outer shell 30 at all. In another embodiment, outer shell 30 is impermeable except for the addition of a vent portion such as vent portion 24. Accordingly, the UV assembly 40 is situated in the interior area (or adjacent the interior area of the rain hood 50 as described later) defined by the walls of the body shell 20 and is operable to kill and destroy germs that are in the airstream passing through the vent portion 40. More particularly, the UV light assembly 40 may include a UV housing 41 and at least a pair of wing members 41a structurally coupled to and extending laterally and rearwardly away from the UV housing. The wing members may include at least one a, preferably, a plurality of light emitters. A UV light 42, appropriate controller 45, and a power source 43 (such as a battery) in electrical communication with the UV light are situated in the UV housing 41. An on/off button 43a for actuating the power source 43 and light 42 may also be included. Further, the UV light assembly 40 may include a plurality of light bands 44 (e.g., light tubes) may be positioned and extend through the wing members 41a (FIG. 9a) and are in fluid communication with the UV light 42. In a critical aspect, the wing members 41a are immediately adjacent or, at least, proximate the vent portion 24 of the body shell 20 such that the potentially infected ambient airstream is exposed to the UV light when activated to emit through the light bands 44. The UV light assembly 40 includes a UV front section comprising the UV housing 41 and UV side sections comprising the plurality of light bands 44, wherein said UV side sections are angled rearwardly and outwardly away from said UV housing 41 and are immediately adjacent and coincide in shape with the vent side sections so as to be nested therewith, as seen in FIGS. 1b, 4b, and 5. The electrical components described above are shown in FIG. 10. The UV light assembly 40 may include a UV light cover 46 having a configuration that is identical or complementary to that of the UV housing 41 and pair of wing members 41a, the UV light cover 46 being positioned rearwardly of the housing and wing members so as to protect them from direct contact with a user's nose when the facemask assembly 10 is worn (FIG. 4b).

In another critical aspect, the facemask assembly 10 may include a rain shield 50 that is operable as a protective barrier against weather elements such as rain. The rain shield 50 may also be referred to as a rain hood 50. The rain shield 50 may include a center panel 52 that stands upright and a pair of shield side sections 54 coupled to the center panel 52 and extending outwardly and rearwardly, respectively. Again, the rain shield presents an upstanding center wall and a pair of side sections that extend rearwardly like the wings of an airplane. As shown in FIGS. 4a and 4b, the center panel 52 and shield side sections 54 each includes a receiver portion 55 that is angled or bent inwardly and configured to receive the outer shell 30 and a friction fit and nested relationship. Preferably, the rain shield 50 is constructed of a material that is moisture resistant or water impermeable, such as metal, plastic, Plexiglas, or the like.

Figure 2:
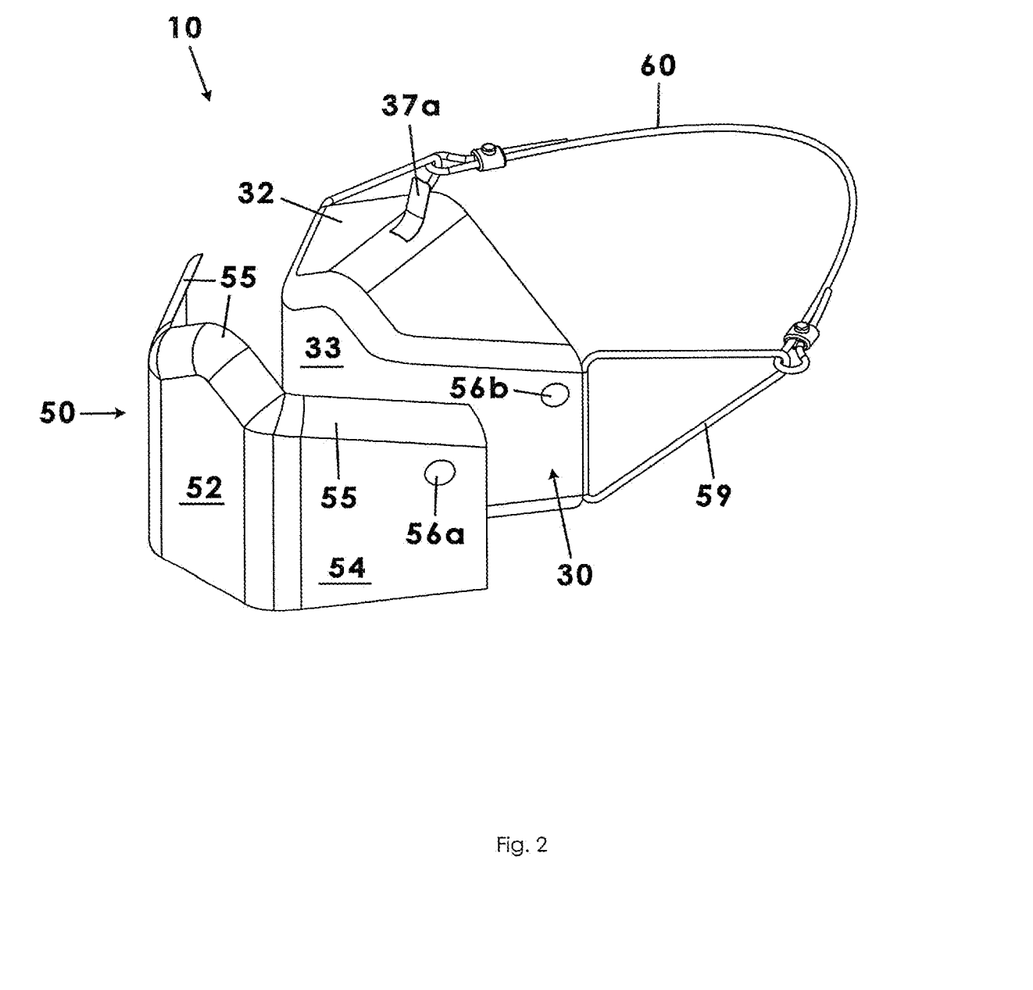
FIG. 2 is a partially exploded view of the facemask assembly as in Fig. 1a also illustrating a rain shield according to the present invention.

The rain shield 50 may be removably coupled to a front of the outer shell 30 so as to protect the outer shield from moisture. Either of two embodiments of the rain shield 50 are immediately contemplated and both will be described below. In one embodiment, the rain shield 50 and the outer shell 30 each include at least one embedded magnet, the magnets being oriented to have opposite polarities that are magnetically attracted to one another. FIG. 2 is an exploded view that illustrates a first magnet 56a embedded in a side section 54 and a second magnet 56b embedded in a side section of an outer shell 30. It is understood that the magnets may be aligned such that a rain shield 50 may be quickly and easily coupled to a corresponding outer shell 30 and to remain in a desired orientation until gentle pressure by a user is used to displace the two components.

Figure 3B:
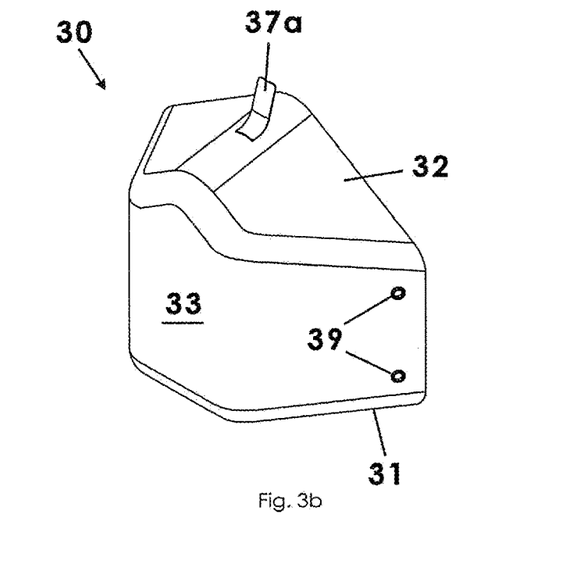
FIG. 3b is an isolated perspective view of the outer shell according to an embodiment of the present invention.

In another embodiment, each side section 54 of the rain shield 50 may define an eyelet 58, e.g., an opening suitable for receiving a cord or, in the context of the present invention, the head or neck strap 60, which will be described later in more detail (FIG. 4a). Similarly, the outer shell 30 and body shell 20 may define eyelets 39, 29, respectively, as shown in FIGS. 3a and 4b. It is understood that all of the eyelets described above are aligned such that respective ends of the head or neck strap 60 may be passed through the eyelets simultaneously not only to secure the strap 60 to the facemask assembly 10 but also to hold the layers of the assembly together more securely. It is also understood that embodiments may define multiple and distributed eyelets 29 to enhance securing of the strap 60 (FIG. 3b).

As described above, the facemask assembly 10 includes a strap 60 for coupling the facemask assembly 10 to a user's ears, neck, or the like. In the embodiment that defines aligned eyelets, opposed ends of the strap 60 may be inserted through respective eyelets (FIG. 4a). The remainder of the strap 60 has a continuous configuration and may be hooked behind a user's neck or ears so that respective rearward edges of body shell 20 and of the outer shell 30 so as to cover the user's nose and mouth.

By contrast, in the embodiment having embedded magnets 56a, 56b, strap loops 59 may be mounted to opposite rearward edges of the body shell 20 (or, in an embodiment, mounted to rearward edges of the outer shell 30). Then, opposed ends of the strap 60 may be coupled to respective strap loops 59. Again, the remainder of the strap 60 has a continuous configuration and may be hooked behind a user's neck or ears so that respective rearward edges of body shell 20 and of the outer shell 30 cover the user's nose and mouth.

Figure 7A:
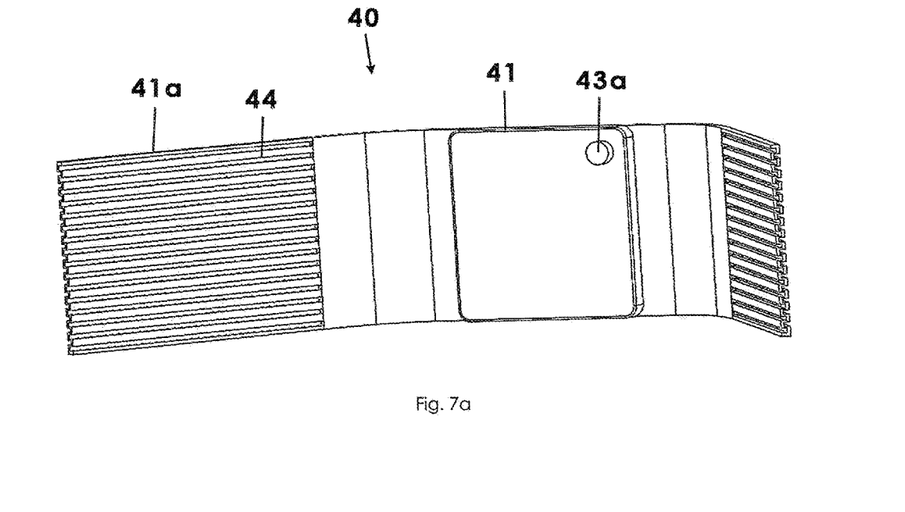
FIG. 7a is a front view of the ultraviolet light assembly according to the present invention.
Figure 7B:
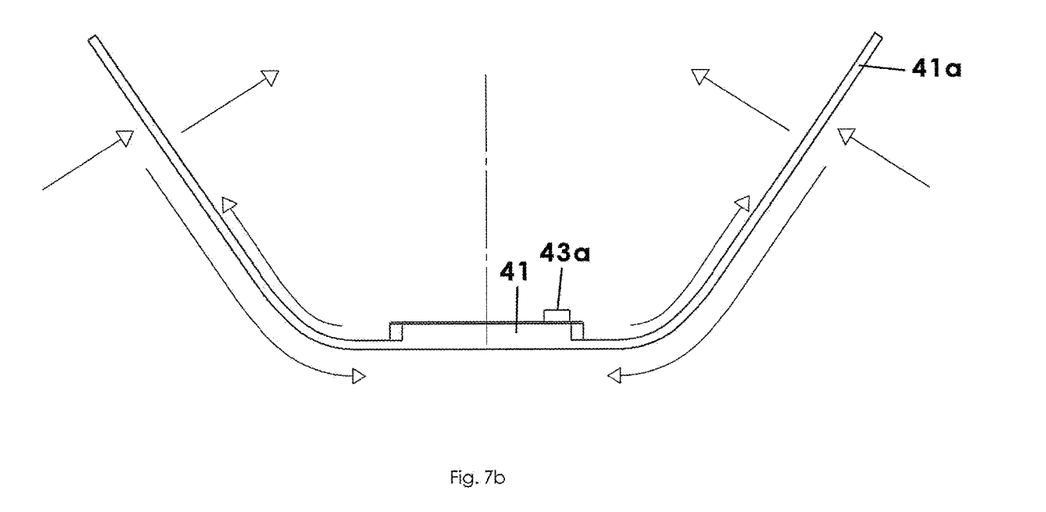
Figure 8A:
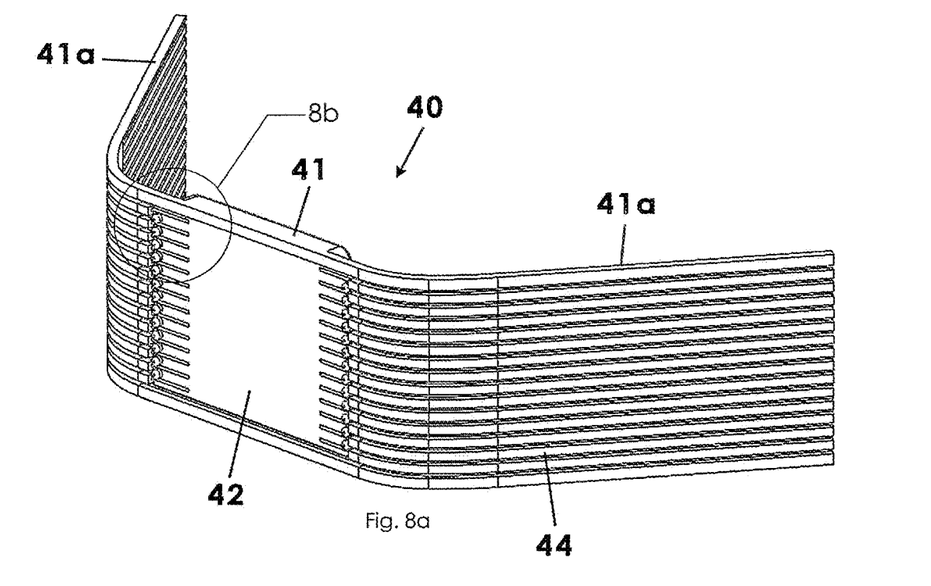
Figure 8B:
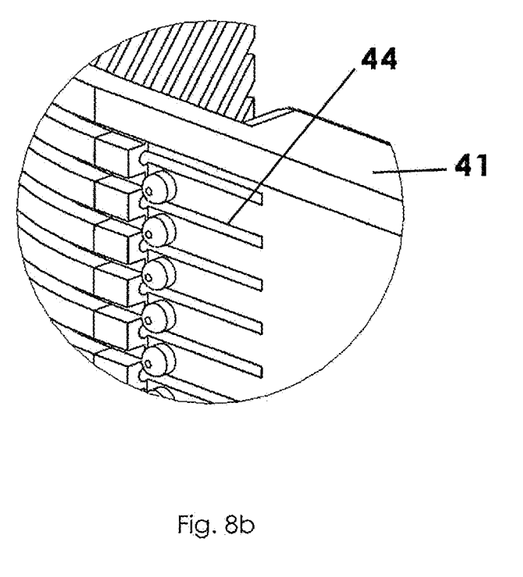
Figure 9A:
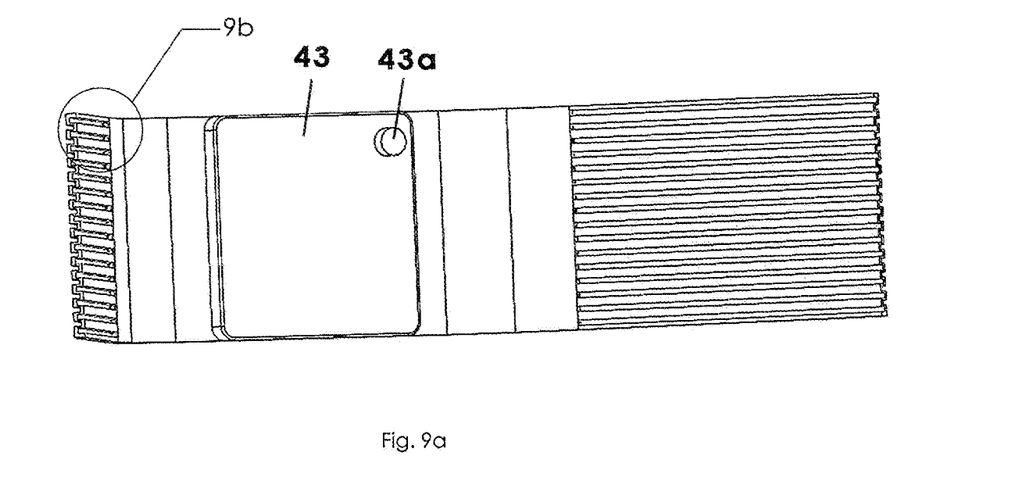
Figure 9B:
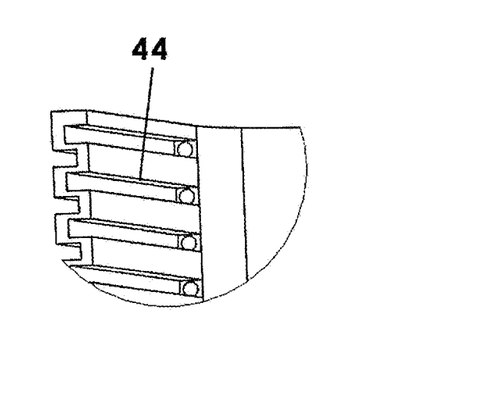
Figure 10:
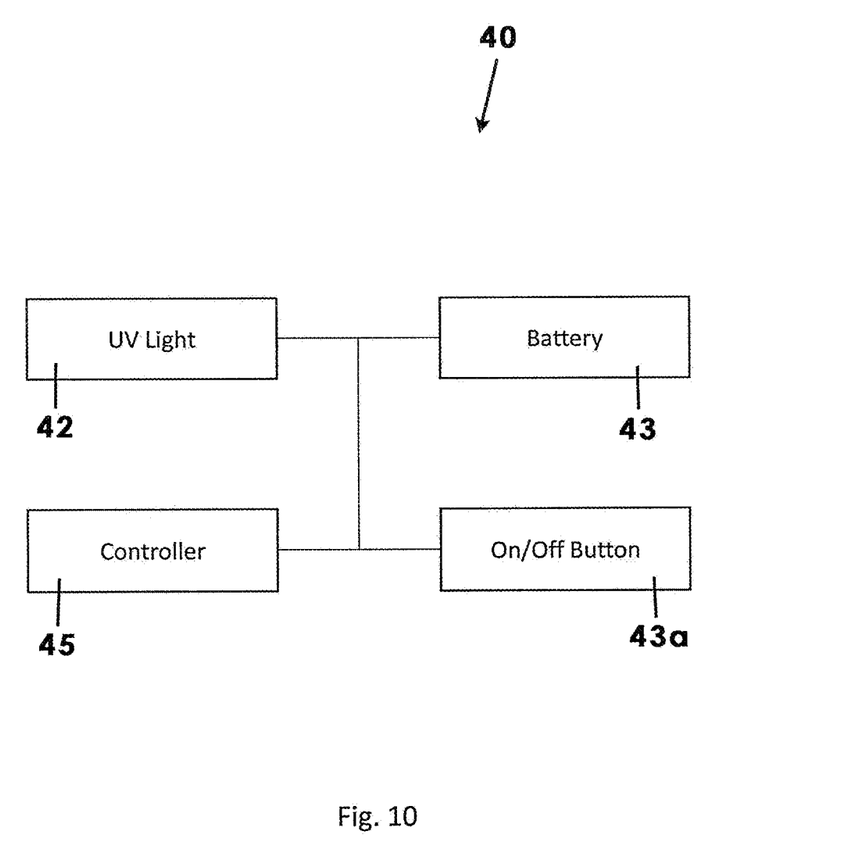
FIG. 10 is a flowchart schematically illustrating the electronic components of the present invention.

In use, the body shell 20 may be nested and coupled inside the outer shell 30 at the point of manufacturing as well as mounting of the strap 60 such that facemask assembly 10 is ready to be worn by a user as described above. The rain shield 50 may be coupled to the front of the outer shell 30 when protection from weather elements is desired. FIG. 7b illustrates how an airstream flows through the ultraviolet light assembly 40 before being inhaled through the nose or mouth of a user. More particularly, the side wings 41a of housing 41 are impermeable to the ambient airstream and, thus, the airstream is directed to the UV chamber situated between the side wings 41a as shown in FIG. 7b. The airstream is directed through the light bands 44 in which it is exposed to ultraviolet light and cleansed. Only then, is the airstream able to be inhaled by a user.

It is understood that while certain forms of this invention have been illustrated and described, it is not limited thereto except insofar as such limitations are included in the following claims and allowable functional equivalents thereof.

The invention claimed is:
1. A three-dimensional face mask assembly, comprising:
a body shell including a body bottom wall, a body top wall parallel to said body bottom wall, and a body front wall extending between said body bottom wall and said body top wall, wherein said body front wall includes a body front section and a pair of body side sections each being angled rearwardly and outwardly away from said body front section, and configured to contact a wearer's face in a straight edge configuration along the wearer's cheeks, said body bottom wall, said body top wall, and a portion of said body front wall being constructed of an air impermeable material;

said body bottom wall, said body top wall, and said body front wall, together, define a body interior area;

wherein said body front wall includes a vent portion constructed of an air permeable material, the vent portion having a vent front section and a pair of vent side sections angled rearwardly and outwardly away from said vent front section to coincide with the body front section and pair of body side sections, respectively;

an outer shell including an outer shell bottom wall, an outer shell top wall parallel to said outer shell bottom wall, and an outer shell front wall extending between said outer shell bottom wall and said outer shell top wall, said outer shell bottom wall, said outer shell top wall, and said outer shell front wall, together, define an outer shell interior area that is configured to receive said body shell in a nested arrangement;

wherein said outer shell bottom wall, said outer shell top wall, and said outer shell front wall being constructed of a fabric material that is air permeable;

an ultraviolet ("UV") light assembly positioned immediately adjacent said vent portion in said body interior area, said UV light assembly including a UV front section comprising a UV housing and UV side sections comprising a plurality of light bands, wherein said UV side sections are angled rearwardly and outwardly away from said UV housing and are immediately adjacent and coincide in shape with the vent side sections so as to be nested therewith, said UV light assembly being operable to produce electromagnetic energy, when actuated, so as to be capable of suppressing germs.

2. The facemask assembly as in claim 1, wherein said UV light assembly includes:
the plurality of light bands extending along said vent portion;
a controller, a power source, and at least one UV light configured to emit UV light when energized, said at least one UV light being in fluid communication with said vent portion and situated such that ambient air flowing through said vent portion is subjected to said UV light when energized.

3. The facemask assembly as in claim 2, further comprising a UV light cover having a front surface that is coupled to a rear surface of said UV housing, said UV light cover having a configuration that is complementary to a configuration of said UV housing.

4. The facemask assembly as in claim 1, wherein said outer shell and said body shell have configurations that are concentric, said body front wall of said body shell being coupled to an interior surface of said outer shell front wall of said outer shell.

5. The facemask assembly as in claim 4, further comprising a strap having opposed ends each coupled to opposed rear edges of said outer shell, respectively.

6. The facemask assembly as in claim 1, wherein:
said body top wall has an inverted V-shaped configuration; and
said body bottom wall, said body top wall, and said body front wall include rear edges, respectively, having a profile that can cover a nose and mouth of the wearer.

7. The facemask assembly as in claim 6, wherein said outer shell top wall includes a pull-tab having a distal portion extending away and that is capable of being grasped and pulled upwardly to said inverted V-shaped configuration.

8. The facemask assembly as in claim 1, further comprising a rain shield having a center panel and a pair of shield side sections each being angled rearwardly and outwardly away from said center panel, said rain shield having a configuration that is complementary to a configuration of said outer shell and is releasably coupled to a front surface of said outer shell.

9. The facemask assembly as in claim 8, wherein said rain shield is constructed of a water impermeable material.

10. A three-dimensional face mask assembly, comprising:
a body shell including a body bottom wall, a body top wall parallel to said body bottom wall, and a body front wall extending between said body bottom wall and said body top wall, wherein said body front wall includes a body front section and a pair of body side sections each being angled rearwardly and outwardly away from said body front section, and configured to contact a wearer's face in a straight edge configuration along the wearer's cheeks, said body bottom wall, said body top wall, and a portion of said body front wall being constructed of a material that is impermeable to ambient air;

said body bottom wall, said body top wall, and said body front wall, together, define an open rear end and a body interior area;

wherein said body front wall includes a vent portion that extends laterally between opposed ends of said body front wall and that is permeable to ambient airflow, the vent portion having a vent front section and a pair of vent side sections angled rearwardly and outwardly away from said vent front section to coincide with the body front section and pair of body side sections, respectively;

an outer shell including an outer shell bottom wall, an outer shell top wall parallel to said outer shell bottom wall, and an outer shell front wall extending between said outer shell bottom wall and said outer shell top wall, said outer shell bottom wall, said outer shell top wall, and said outer shell front wall, together, define an open outer shell rear end and an outer shell interior area that is configured to receive said body shell in a nested arrangement;

wherein said outer shell bottom wall, said outer shell top wall, and said outer shell front wall is constructed of a fabric material that is permeable to an ambient airflow;

a rain shield having a center panel and a pair of shield side sections each being angled rearwardly and outwardly away from said center panel, said rain shield having a configuration that is complementary to a configuration of said outer shell and is releasably coupled to a front surface of said outer shell, wherein said rain shield is constructed of a water impermeable materials;

an ultraviolet ("UV") light assembly positioned immediately adjacent said vent portion in said body interior area, said UV light assembly including a UV front section comprising a UV housing and UV side sections comprising a plurality of light bands, wherein said UV side sections are angled rearwardly and outwardly away from said UV housing and are immediately adjacent and coincide in shape with the vent side sections so as to be nested therewith, said UV light assembly being operable to produce electromagnetic energy, when actuated, so as to be capable of suppressing germs.

11. The facemask assembly as in claim 10, wherein:
said outer shell front wall includes a pair of outer shell side sections each being angled rearwardly and outwardly from an outer shell center section;
a first pair of magnets situated on said pair of outer shell side sections, respectively, of said outer shell:
a second pair of magnets situated on said pair of shield side sections, respectively, of said rain shield, said second pair of magnets being aligned and in reverse polarity with said first pair of magnets so as to be magnetically attracted therewith when said rain shield is coupled to said outer shell.

12. The facemask assembly as in claim 11, further comprising:
a pair of loop fasteners coupled to a pair of oppositely disposed rear edges of said outer shell front wall side sections, respectively; and
a strap having opposed ends each coupled to said pair of loop fasteners, respectively.

13. The facemask assembly as in claim 10, wherein:
said body top wall has an inverted V-shaped configuration and is constructed of semi-flexible material; and
said body bottom wall, said body top wall, and said body front wall include rear edges, respectively, having a profile that can cover a nose and mouth of the wearer.

14. The facemask assembly as in claim 13, wherein said outer shell top wall includes a pull-tab having a distal portion extending away and that is capable of being grasped and pulled upwardly to said inverted V-shaped configuration.

15. The facemask assembly as in claim 10, wherein said UV light assembly includes:
the UV side sections forming a pair of wing members extending laterally away from said UV housing along said vent portion;
a controller, a battery, and a UV light situated in said UV housing; and
wherein the plurality of light bands are in fluid communication with said vent portion and situated in said pair of wing members such that ambient air flowing through said plurality of light bands is subjected to UV light waves when said UV light is energized by said battery.

16. The facemask assembly as in claim 15, further comprising a UV light cover having a front surface that is coupled to a rear surface of said UV light assembly, said UV light cover having a configuration that is complementary to a configuration of said UV housing and said pair of wing members, respectively.

17. The facemask assembly as in claim 10, wherein:
said outer shell front wall includes an outer shell center section and a pair of outer shell side sections each being angled rearwardly and outwardly from said outer shell center section;
said pair of outer shell side sections each defining an outer shell eyelet opening, respectively;
said pair of rain shield side sections each defining a rain shield eyelet opening, respectively, said pair of outer shell eyelet openings being aligned with said pair of rain shield eyelet openings;
said facemask assembly comprising a strap having opposed ends, said each rain shield eyelet opening and each outer shell eyelet opening being configured to receive an opposed end of said strap when said rain shield is coupled to said outer shell to enhance the coupling of said rain shield to said outer shell.

* * * * *